United States Patent [19]
May

[11] Patent Number: 5,847,134
[45] Date of Patent: Dec. 8, 1998

[54] FLUOROCARBON-CONTAINING ISOCYANATE DERIVATIVES AND SOIL-RESIST AGENTS

[75] Inventor: Donald Douglas May, Chadds Ford, Pa.

[73] Assignee: E. I. du Pont de Nemours and Company, Wilmington, Del.

[21] Appl. No.: 585,339

[22] Filed: Jan. 11, 1996

[51] Int. Cl.$^6$ ............... C07D 251/32; C07C 273/02; C08G 18/10
[52] U.S. Cl. .............. 544/222; 560/25; 560/26; 560/27; 562/439; 564/38; 528/59; 252/182.2
[58] Field of Search ............... 564/38; 562/439; 560/25, 26, 27; 544/222; 528/59; 252/182.2

[56] References Cited

U.S. PATENT DOCUMENTS

| | | | |
|---|---|---|---|
| 3,283,012 | 11/1966 | Day | 568/842 |
| 3,378,609 | 4/1968 | Fasick et al. | 525/227 |
| 3,462,296 | 8/1969 | Raynolds et al. | 427/381 |
| 3,491,169 | 1/1970 | Raynolds et al. | 525/160 |
| 3,923,715 | 12/1975 | Dettre et al. | 524/199 |
| 4,595,518 | 6/1986 | Raynolds et al. | 427/393.4 |
| 4,958,039 | 9/1990 | Pechhold | 556/421 |
| 5,097,090 | 3/1992 | Beck | 568/842 |
| 5,408,010 | 4/1995 | May | 525/327.4 |
| 5,414,111 | 5/1995 | Kirchner, Jr. | 560/357 |
| 5,427,859 | 6/1995 | May | 428/421 |

FOREIGN PATENT DOCUMENTS

| | | |
|---|---|---|
| 0 435 641 A | 7/1991 | European Pat. Off. . |
| 0 540 976 A | 5/1993 | European Pat. Off. . |

OTHER PUBLICATIONS

Edited By Gunter Oertel, Polyurethane, *Principles of Polyurethane Chemistry and Special Applications*, 2ND Edition, 21–23; 48, 1995.

*Primary Examiner*—John Kight
*Assistant Examiner*—D. Margaret M. Mach

[57] ABSTRACT

Products prepared by reacting polyisocyanates with alkenyl or alkynyl compounds; then with perfluoroalkyl iodides & dehydroiodinating the product.

16 Claims, No Drawings

FLUOROCARBON-CONTAINING ISOCYANATE DERIVATIVES AND SOIL-RESIST AGENTS

FIELD OF THE INVENTION

This invention relates to novel perfluoroalkyl substituted derivatives of isocyanates, processes for preparing the same, and soil-resist agents thereof.

BACKGROUND OF THE INVENTION

Several of the currently-used soil-resist agents for nylon carpets are based on polymers derived from perfluoroalkylethyl alcohols. The perfluoroalkylethyl alcohols can be prepared from perfluoroalkyl iodides by sequentially reacting with ethylene to form the corresponding perfluoroalkylethyl iodides, then with oleum to form perfluoroalkylethyl sulfates, followed by conversion to the perfluoroalkylethyl alcohols by hydrolysis (see U.S. Pat. Nos. 3,283,012 and 5,097,090). The perfluoroalkylethyl alcohols are converted to monomers, incorporated into polymers, and applied to the fiber substrates (see U.S. Pat. Nos. 3,378,609, 3,462,296, 3,491,169, 4,595,518, 3,923,715, and 4,958,039). The prior art technology has a number of drawbacks. It involves several steps in which the expensive perfluorocarbon moiety is subject to yield and handling losses; pressure equipment is required for some of the steps, and large quantities of by-product sulfuric acid are formed and require disposal. It would be desirable if a suitable perfluorocarbon-derived soil-resist could be prepared more directly from the perfluoroalkyl iodides without the disadvantages of the currently-used and multiple-step technology described above.

More recently, my U.S. Pat. No. 5,408,010 disclosed a method for the direct use of perfluoroalkyl iodides to make soil-resists without the preparation of the intermediate perfluoroalkylethyl alcohols; i.e. the use of a product made by reacting a performed styrene/maleic anhydride copolymer sequentially with an allylic compound and then with perfluoroalkyl iodides. The perfluoroalkyl-substituted product is applied to the fiber substrate from aqueous emulsion.

BRIEF SUMMARY OF THE INVENTION

The present invention relates to the novel products prepared by the sequential reaction of polyisocyanates with terminally unsaturated alkenyl or alkynyl Zerewitinoff hydrogen-containing compounds; then perfluoroalkylating the alkenylated or alkynylated polyisocyanates by reaction with perfluoroalkyl iodides and finally dehydroiodinating the product so as to effect elimination of hydrogen iodide therefrom. The resulting compositions are readily emulsified in water and have utility as soil-resist agents.

DETAILED DESCRIPTION OF THE INVENTION

The novel compositions of this invention are made in a sequence of two to four steps summarized below and subsequently described in greater detail:

1. ALKENYLATION or ALKYNYLATION—Polyisocyanates containing 2 or more reactive isocyanate groups, were dissolved in suitable solvents, then were reacted with terminally unsaturated alkenyl or alkynyl compounds. The terminally unsaturated alkenyl or alkynyl compounds with which the polyisocyanates of this invention are reacted include but are not limited to, allyl amine, diallyl amine, allyl mercaptan, allyl alcohol, $CH_2=CH(CH_2)_q-OH$, or propargyl alcohol 2. OPTIONALLY—The polyisocyanates can be extended, before or after alkenylation or alkynylation by reaction of a part of their reactive isocyanate functionality with known extenders.

3. PERFLUOROALKYLATION and DEHYDROIODINATION—The alkenyl- or alkynyl-substituted polyisocyanate product is reacted with perfluoroalkyl iodide in the presence either an organic peroxide or azo initiator. Residual hydrogen iodide and any free iodine can be removed from the product by washing with base or by reduction.

4. OPTIONALLY—The perfluoroalkylated product in organic solvent solution can be separated from the aqueous buffer phase, emulsified with water containing an emulsifying agent, and the organic solvent removed by distillation under reduced pressure to give an aqueous emulsion of the soil-resist which is standardized and applied to nylon carpet by conventional application techniques. Any active isocyanate groups remaining after extension in Step 3 or emulsification in Step 4 will react with water. The polyisocyanate, or extended polyisocyanate, is reacted completely with a terminal allyl Zerewitinoff hydrogen-containing compound, or partially when that step is followed by extension of the isocyanate. The use of an aqueous buffer in reacting a perfluoroalkyl iodide with an unsaturated compound is disclosed and claimed in my application filed of even date herewith (Attorney Docket No. CH-2316).

Hereinafter the partial reaction of isocyanates or polyisocyanates with water, ammonia, glycols, polyols, diamines, polyamines or the terminal hydroxyl groups of polyesters, polyethers or polyacrylics, is referred to as extension of the isocyanate, the reactant used is referred to as an extender, and the reaction product is referred to as an extended isocyanate. Procedures for extending isocyanates are well known in the art. Procedures for extending isocyanates are well known in the art, e.g. "POLYURETHANE", 2nd Edition, edited by G. Oertel, Hanser/Gardner Publications, Inc. Cincinnati, Ohio (1994), particularly pages 21 through 24; see also U.S. Pat. Nos. 3,124,605 and 5,414,111.

STEP 1—ALKENYLATION

In an illustrative embodiment, to a reaction vessel equipped with agitation, means of addition, means of temperature measurement and control, and equipped with means for maintaining a dry atmosphere, is added an aliphatic or aromatic polyisocyanate, dissolved in a suitable dry solvent, exemplified by, but not limited to, ketones such as methyl isobutyl ketone (4-methyl-2-pentanone) or methyl isoamyl ketone (4-methyl-2-hexanone), hydrocarbons such as toluene or xylene, esters such as ethyl acetate, butyl acetate, or ether-esters such as propylene glycol methyl ether acetate (PMA, 1-methoxy-2-propyl acetate) or the like. The polyisocyanate is reacted with an allylic reactant, exemplified by, but not limited to, allyl amine (2-propene-1-amine), diallyl amine (N-2-propenyl-2-propene-1-amine), allyl alcohol (2-propene-1-ol), and allyl mercaptan (2-propene-1-thiol). The amount of allylic reactant used is 30–100% of the amount necessary to react with all available free isocyanate groups. The lower allylic reactant proportions give an intermediate product which may be further extended before perfluoroalkylation to increase the molecular weight of the soil-resist, a property which can increase the shampoo/cleaning durability of the soil-resist but which, in the perfluoroalkylation step, will react with proportionally less perfluoroalkyl iodide, necessitating higher loading of the soil-resist to the carpet to achieve the required loading of fluorine on the carpet, typically 500–1000 ppm fluorine based on the weight of the carpet. Alternatively, higher allylic reactant proportions give an intermediate product which is less extendible, or unextendable, but will react more extensively with the perfluoralkyl iodide giving a soil-resist with higher fluorine content and requiring lower application rates. The solution is stirred and heated, for instance at 90° C. for four hours, until quantitative gas chromatographic analysis shows less than 1% of the initially-charged allyl compound remaining.

Alternatively the initial polyisocyanate may be an extended polyisocyanate dissolved in the same groups of solvents, performed by standard techniques by reacting a polyisocyanate with about one third of a molecular proportion of water, or about one half a molecular proportion of ammonia, a glycol, or a diamine, or with about reciprocal n molecular proportions of a polyol or polyamine having n hydroxy or amino groups, using methods such as those previously cited by Wagner in U.S. Pat. No. 3,124,605.

Any polyisocyanate having two or more isocyanate groups can be used for the purposes of this invention. For example, one can use hexamethylene diisocyanate (HMDI, 1,6-diisocyanato-hexane), toluene diisocyanate (TDI, a mixture of 2,4-diisocyanato-1-methylbenzene and 1,3-diisocyanato-2-methylbenzene), or HMDI homopolymers having the formula:

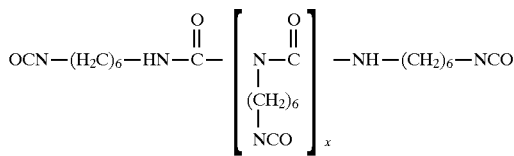

wherein x is an integer equal to or greater than 1, preferably between 1 and 8. Because of their commercial availability, mixtures of such hexamethylene (HMDI) diisocyanate homopolymers are preferred for purposes of this invention. Also of interest are hydrocarbon diisocyanate-derived isocyanurate trimers which can be represented by the formula:

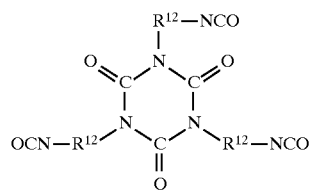

wherein $R^{12}$ is a divalent hydrocarbon group, preferably aliphatic, alicyclic, aromatic or arylaliphatic. For example, $R^{12}$ can be hexamethylene, toluene or cyclohexylene, preferably the former. Other polyisocyanates useful for the purposes of this invention are those obtained by reacting three mols of toluene diisocyanate with 1,1,1-tris-(hydroxymethyl)-ethane or 1,1,1-tris-(hydroxymethyl)-propane. The isocyanate trimer of toluene diisocyanate and that of 3-isocyanatomethyl-3,4,4-trimethylcyclohexyl isocyanate are other examples of polyisocyanates useful for the purposes of this invention, as is methine-tris-(phenylisocyanate). Also useful for the purposes of this invention is the polyisocyanate having the formula:

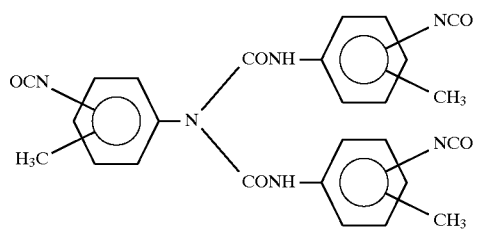

"DESMODUR N-100" and "DESMODUR 3200" are hexamethylene diisocyanate homopolymers commercially available from the Bayer Corporation. Both presumably are prepared by the process described in U.S. Pat. No. 3,124,605 and presumably to give mixtures of the mono, bis, tris, tetra and higher order derivatives which can be represented by the general formula:

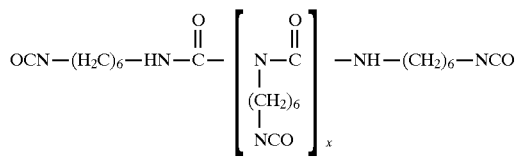

wherein x is an integer equal to or greater than 1, preferably between 1 and 8.

| Typical Properties | Ave. Eq. Wt. | NCO Content, % |
| --- | --- | --- |
| "DESMODUR N-100" | 191 | 22.0 |
| "DESMODUR 3200" | 181 | 23.2 |

The typical NCO content of "DESMODUR N-100" approximates that listed for a SRI International Report (Isocyanates No. 1D, July, 1983, Page 279) hexamethylene diisocyanate homopolymer with the following composition:

| Product Composition | Wt. % |
| --- | --- |
| Hexamethylene diisocyanate | 0.1 |
| Monobiuret | 44.5 |
| Bisbiuret | 17.4 |
| Trisbiuret | 9.5 |
| Tetrabiuret | 5.4 |
| Higher Mol. Wt. Derivatives | 23.1 |
| NCO Content | 21.8 |

Based on its average equivalent weight and NCO content, the comparative bis, tris, tetra, etc., content of "DESMODUR 3200" should be less than that of the N-100 product. "DESMODUR N-3300" is a hexamethylene diisocyanate-derived isocyanurate trimer which can be represented by the formula:

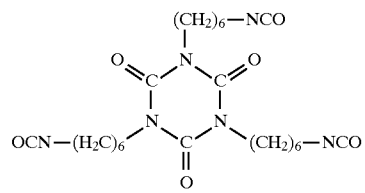

Preformed commercially available extended polyisocyanates are exemplified by, but not limited to, American Cyanamid's "CYTHANE 3160"; Bayer's "DESMODUR 3300"; "DESMODUR 3200"; & "DESMODUR N-100"; and isophorone. "CYTHANE" is a polyisocyanate having the formula:

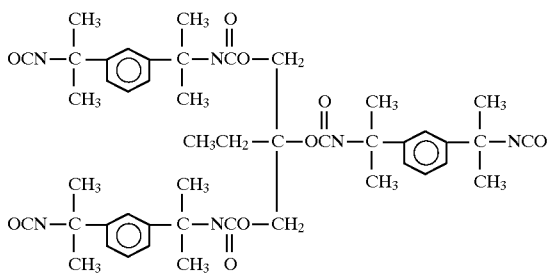

Aromatic isocyanates and extended aromatic isocyanates in which the isocyanate group is directly attached to an aromatic ring are less preferred due to their pronounced tendency to yellow on exposure to ambient ultraviolet light. Examples of these less preferred polyisocyanates are toluene diisocyanates (TDI, a mixture of 2,4 -diisocyanato-1-methylbenzene and 1,3-diisocyanato-2-methylbenzene) and 1,1'-methylenebis(4-isocyanatobenzene) (MDI).

STEP 2—EXTENSION OF THE SOIL-RESIST INTERMEDIATE

Optionally, when the proportion of the allyl reactant is less than 100% of the equivalent weight, based on the available free isocyanate groups, the allyl-substituted isocyanate product may be further extended or crosslinked in the same reaction vessel with water, ammonia, a glycol, a diamine, a polyol, polyamine, or the terminal hydroxyls of a polyester, polyether or polyacrylic.

STEP 3—PERFLUOROALKYLATION AND DEHYDROIODINATION

In the same reaction vessel, the solution of the allyl-substituted isocyanate product in the solvent described in Step 1 is mixed with an aqueous buffered solution of pH 2–8, preferably pH 3–6, and optimally with an buffered aqueous solution containing about 5% sodium hydroxide and 10% acetic acid having a pH of about 4. Other buffered systems include any of the following combinations: an alkali metal succinate and borax, an alkali metal succinate and succinic acid, an alkali metal hydroxides and an alkali metal carbonate, and an alkali metal hydroxide and an alkali metal bicarbonate. While the proportions of the various combinations set forth above will affect the final pH of the system, any amount of each of the components of those combinations will cause the pH of the buffered system to fall into an acceptable pH range. As an alternative to the buffered phase, an aqueous phase may be used with a means for continuously measuring and adjusting the pH of the aqueous phase. A base, exemplified by but not limited to, alkali metal hydroxides or alkaline earth metal hydroxides, such as sodium hydroxide or potassium hydroxide, is added to the aqueous phase, either manually or preferentially by means of an automated pump controlled by the pH signal, so as to maintain the pH in the range 2–8, and preferably 3–6, during the perfluoroalkylation.

The aqueous buffer or the pH-controlled aqueous phase, is a necessary part of this invention to achieve rapid and complete reaction with the perfluoroalkyl iodide. During this perfluoroalkylation step some hydrogen iodide is eliminated, forming small amounts of free iodine. Free iodine inhibits the perfluoroalkylation. The aqueous phase buffer serves to maintain a pH high enough to suppress iodine formation and to scavenge any hydrogen iodide and iodine formed. Too high a pH causes hydrolysis of the perfluoroalkyl iodides with the formation of inert products such as the perfluoroalkyl hydrides, too low a pH results in incomplete scavenging of hydroiodic acid and iodine by-products and termination of the perfluoroalkylation addition.

To the stirred two-phase system comprising the solution of allyl-substituted isocyanate in solvent and the buffered aqueous solution and under an inert gas atmosphere to exclude oxygen, is immediately added a perfluoroalkyl iodide or mixture of perfluoroalkyl iodides.

The perfluoroalkyl iodide may be either a single perfluoroalkyl iodide or a mixture of perfluoroalkyl iodides. Typically the Rf radical is a straight chain fluoroalkyl residue containing 4 to 20 carbon atoms or a mixture of such iodides may be employed. Preferably, the Rf radical contains about 4 to 16 carbon atoms. The iodide may also include a substituent Y which may be F, Cl, Br or H, although F is preferred. In a more preferred embodiment, one uses a mixture of perfluoroalkyl iodides having the formula:

$$F(CF_2)_a I$$

wherein a is predominantly 6, 8 and 10. In a typical mixture, hereinafter Perfluoroalkyl Iodide Mixture A, the compounds will have the following approximate composition in relation to their $F(CF_2)a$ radicals:

0% to 3% wherein a=4,
27% to 37% wherein a=6,
28% to 32% wherein a=8,
14% to 20% wherein a=10,
8% to 13% wherein a=12,
3% to 6% wherein a=14,
0% to 2% wherein a=16,
0% to 1% wherein a=18, and
0% to 1% wherein a=20.

Other fluorochemical reagents which can be used include a perfluoroalkyl iodide mixture of the formula shown below wherein a is predominantly 8, 10 and 12. In a typical mixture of such fluoroalkyl iodides, hereinafter Perfluoroalkyl Iodide Mixture B, the compounds will have the following approximate composition in relation to their $F(CF_2)_a$ radicals:

0% to 3% wherein a=6,
45% to 52% wherein a=8,
26% to 32% wherein a=10,
10% to 14% wherein a=12,
2% to 5% wherein a=14,
0% to 2% wherein a=16,
0% to 1% wherein a=18, and
0% to 1% wherein a=20.

About 0.5 weight % of an organic peroxide initiator, exemplified by, but not limited to, t-butyl peroctanoate (2-ethylhexaneperoxoic acid, 1,1-dimethylethyl ester, from Lucidol Pennwalt Chemicals) or a "VAZO 67" initiator, exemplified by, but not limited to, "VAZO 67" (2,2'-azobis [2-methylbutyronitrile] and "VAZO 64" 2,2'-azobis[2-methylpropane-nitrile, both from DuPont), based on the weight of the perfluoroalkyl iodide, is added. The reactants are stirred at a temperature such that the initiator will have a half-life of about 2–4 hours. A second 0.5% portion of the initiator is added after about three hours. Tables of initiator half lives are provided by initiator manufacturers. Reaction temperatures would be 75°–90° C. for t-butyl peroctanoate and for "VAZO 67". The use of "VAZO 67" in methyl isobutyl ketone at 90° C. is particularly preferred as this is the boiling point of the methyl isobutyl ketone-water azeotrope, affording convenient temperature control. The temperature and stirring are continued until this step is completed, at which stage the absence of unreacted perfluoroalkyl iodide can be demonstrated by gas chromatography, typically after about 3–6 hours.

STEP 4—PREPARATION OF AN AQUEOUS EMULSION AND APPLICATION

The bottom aqueous phase, containing scavenged inorganic iodide from the reacted perfluoroalkyl iodide, is removed to leave the perfluoroalkyl-substituted product in solution in organic solvent. The organic solvent layer is stirred with a 10% molar excess of dilute base, based on amount of perfluoroalkyl iodide used in the reaction exemplified but not limited to potassium or sodium carbonate to remove hydrogen iodide from the perfluoroalkylated product and the lower aqueous phase containing the bulk of the iodide is removed. The organic phase is washed with water preferentially containing a sufficient quantity of a salt such as sodium chloride or sodium acetate such that the wash solution is of sufficient density to provide easy phase separation. The organic layer is finally washed with water.

An emulsifying agent is selected by customary techniques such as are described by Rosen in Surfactants and Interfacial Phenomena, Wiley-Interscience, New York N.Y., 1978. Examples of preferred emulsifying agents are exemplified by, but not limited to, "ARQUAD 18-50" (N,N,N-trimethyl-1-octadecane-ammonium chloride), "ARQUAD 12-50" (N,N,N-trimethyl-1-dodecane-ammonium chloride), both from Akzo Chemicals, and "SUL-FON-ATE AA-10" (sodium dodecylbenzene sulfonate, from Tennessee Chemical Company). Preferred emulsification temperatures are about 40° C. to 90° C., most preferably about 60° C.

The volatile organic solvent is stripped from the emulsion by distillation under reduced pressure at about 40° C. to 90° C., most preferably about 60° C., to yield an aqueous dispersion of the soil-resist agent. Excessive temperatures during solvent stripping may cause the emulsion to break. The dispersion is standardized by dilution with water to product specifications, typically to a specified fluorine content, applied to nylon carpet by conventional application techniques to provide 500–1000 ppm fluorine based on the fiber weight, and dried in a forced air oven at 225° TO 275° F. (~107° to 135° C.), preferably 250° F. (~120° C.) for 15 to 35 minutes, preferably 25 minutes. The treated carpet may be tested for soil-resistance by the standard tests referenced in AATCC Method 123-1988.

In the examples which follow, the tests described or disclosed below were used to provide oil and water repellency data (O/W) and Drum Soil Screen.

Oil/Water Repellency

Beginning with the lowest numbered test liquid (Repellency Rating No. 1), one drop (approximately 5 mm diameter or 0.05-ml volume) is placed on each of three locations at least 5 mm apart. The drops are observed for 10 seconds for the water-repellency test, 30 seconds for the oil-repellency test. If, at the end of those periods of time, two of the three drops are still spherical to hemispherical in shape with no wicking around the drops, three drops of the next higher numbered test liquid are placed on adjacent sites and observed again for the specified periods of time. The procedure is continued until one of the test liquids results in two of the three drops failing to remain spherical or hemispherical, or wetting or wicking occurs. The oil-repellency rating and the water-repellency rating of the yarn, fabric or carpet each is the highest numbered test liquid for which two of three drops remain spherical or hemispherical with no wicking for the specified time.

| | STANDARD WATER TEST LIQUIDS | |
|---|---|---|
| | Composition (Volume %) | |
| Water-Repellency Rating Number | Isopropanol (Reagent Grade) | Distilled H20 |
| 1 | 2 | 98 |
| 2 | 5 | 96 |
| 3 | 10 | 90 |
| 4 | 20 | 80 |
| 5 | 30 | 70 |

The Drum Soil Screen was carried out in accordance with ASTM 123-1988.

EXAMPLE 1

The preparation of the soil-resist polymers was carried out in a 1 liter resin kettle with bottom outlet, fitted with a 200 rpm mechanical stirrer, a reflux condenser, a thermocouple connected to a PID controller that heats an external resistance heating jacket, and an argon sparge tube; hereafter referred to as Reactor 1. It was charged with 400 g dry methyl isobutyl ketone (MIBK), and 60 g (0.31 eq) of "DESMODUR N-100", (a hexamethylene isocyanate biuret sold by Miles Inc. having the formula:

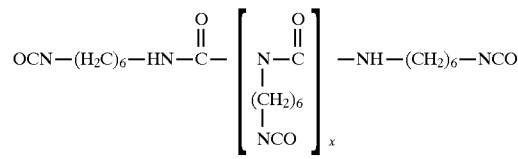

To this was added slowly 30 g (0.30 eq) of diallyl amine (0.30 eq) and the reactor temperature was allowed to go up to 90° C. After addition was complete the contents were stirred for 30 minutes, at which point gas chromatographic analysis showed no unreacted diallyl amine. To the same reaction mixture was added 50 g of a dilute acetate buffer consisting of 5 g concentrated acetic acid, 5 g 50% sodium hydroxide and 40 g water, along with 150 g Perfluoroalkyl Iodide Mixture A. The contents were sparged with nitrogen and, when the temperature of the mixture has again been raised to 90° C., 0.5 g of "VAZO 67" was added. After four hours, gas chromatographic analysis showed no unreacted perfluoroalkyl iodide.

The stirring in reactor 1 was turned off and the contents were allowed to settle and a phase cut taken which contained the aqueous buffer. To the reactor, 100 ml of 20% potassium carbonate were added and the contents stirred at 70° C. for 10 minutes. The stirring was stopped, and another phase cut was taken that contained aqueous iodide. The contents in the reactor were washed again with saturated sodium acetate solution. After the phase cut, the organic phase was added to the following system to make a dispersion.

To make an anionic dispersion, the organic solution described above was added to 600 g of water containing 4.5 g of sodium dodecyl benzene sulfonate in a high shear roto-stator mixer. After addition was complete, the emulsion was passed twice through a two stage Gaulin homogenizer at 3000 psig. After homogenization, the emulsion was distilled under reduced pressure to remove MIBK solvent as a water azeotrope (60° C. at 120 mm) to leave 900 g of a cream colored dispersion that contained 9.5% fluorine by weight (total fluorine accountability 97%). The unimodal particle size of this dispersion was 107 nm with an intensity average of 139 nm. The dispersion, made from base hydrolysis of the Perfluoroalkyl Iodide Mixture A adduct, contained 637 ppm iodide.

To make a cationic dispersion, an organic solution similar to the one described above, except containing only 250 g of dry MIBK, were added to 400 g of water containing 4 g each trimethyl dodecylammonium chloride and trimethyl octadecylammonium chloride at 60° C. in a high shear roto-stator mixer. After addition was complete, the emulsion was passed twice through a two stage Gaulin homogenizer at 3000 psig. After homogenization, the emulsion was distilled under reduced pressure to remove MIBK solvent as a water azeotrope (60° C. at 120 mm) to leave 660 g of a cream colored dispersion that contains 13% fluorine by weight (total fluorine accountability 97%). The unimodal particle size of this dispersion was 112 nm.

Other anionic and cationic surfactants were also used. The characteristics of the dispersions were only slightly different. Each sample was diluted and spray applied to 32 oz stain resist treated level loop nylon carpet at 1000 ppm fluorine. An untreated piece of carpet was used as a control, and all three were placed into a forced hot air oven at 250° F. for 25 minutes. The carpet pieces were tested together by the method described by AATCC Method 123-1988 and the pieces treated with cationic and anionic formulations showed improved resistance to soiling compared to the control.

Comparison Without Acetate Buffer.

The reaction described in Example 1 was repeated except for the omission of acetate buffer. After 4 hrs reaction at 90° C., a sample was taken and showed 105 g unreacted perfluoroalkyl iodide. An additional 0.5 g of "VAZO 67" was added and the contents held at 90° C. for 4 more hours and sampled. There were 100 g of Perfluoroalkyl Iodide Mixture A remaining. Additional amounts of "VAZO 67" were added at 4 hour intervals and the contents heated for 24 total hours to leave 50 g of unreacted perfluoroalkyl iodide in solution, compared with no detectable perfluoroalkyl iodide in the case with acetate buffer, showing the benefit in rate and conversion afforded by the buffer.

EXAMPLE 2

Into reactor 1 were placed 60 g (0.31 eq) "DESMODUR N-100" and 250 g dry MIBK. To the solution was added 20 g (0.20 eq) of diallyl amine and the contents were allowed to heat up to 90° C. and stirred for 30 minutes after addition were complete. Then 5 ml water were added and the contents were stirred for 1 hour. To the same reaction mixture were added 50 g of a dilute acetate buffer consisting of 5 g concentrated acetic acid, 5 g 50% sodium hydroxide and 40 g water, along with 100 g Perfluoroalkyl Iodide Mixture A. The contents were sparged with nitrogen and when the mixture reached 90° C. again from a temperature of about 75° C., 0.5 g of "VAZO 67" was added. After four hours, gas chromatographic analysis showed no unreacted perfluoroalkyl iodide. The contents were worked up as described previously and a cationic dispersion was made. The product was tested as described previously and shows better dry soil and oil and water repellency than the untreated control.

EXAMPLES 3–16

The following examples in Table 1 are illustrative but not exhaustive of the possible chain extended isocyanate based soil-resists that can be prepared. In general, the polyisocyanate was dissolved into MIBK solution functionalized with the number of equivalents of diallyl amine indicated in the table. The resultant prepolymer was chain extended using 0.01 wt % dibutyl tin dilaurate catalyst with the difunctional compounds listed in Table 1. The reaction products were worked up, emulsified, and tested as described in Example 1. In general, cationic dispersion soil-resists performed better in the drum soil screen than anionic ones.

TABLE 1

EXAMPLES 3–16

| No. | Polymer Characteristics | | | Dispersion Characteristics | |
|---|---|---|---|---|---|
| | Isocyanate | Ratio | Extender | Surfactants | Solids |
| 3 | N-100 | 0.67 | a | 3% AA-10 | 50/25/1 |
| 4 | N-100 | 0.67 | a | 3% ARQUAD 12/18 | 50/25/1 |
| 5 | N-100 | 0.67 | b | 3% ARQUAD 12/18 | 50/25/1 |
| 6 | N-100 | 0.67 | b | 3% AA-10 | 50/25/1 |
| 7 | N-100 | 0.67 | c | 3% ARQUAD 12/18 | 50/25/1 |
| 8 | N-100 | 0.67 | c | 3% AA-10 | 50/25/1 |
| 9 | N-100 | 0.67 | d | 3% AA-10 | 50/25/1 |
| 10 | N-100 | 0.67 | d | 3% ARQUAD 12/18 | 50/25/1 |
| 11 | N-100 | 0.67 | e | 3% AA-10 | 50/25/1 |
| 12 | N-100 | 0.67 | e | 3% ARQUAD 12/18 | 50/25/1 |
| 13 | N-100 | 0.67 | f | 3% AA-10 | 50/25/1 |
| 14 | N-100 | 0.67 | f | 3% ARQUAD 12/18 | 50/25/1 |
| 15 | N-100 | 0.67 | g | 3% AA-10 | 50/25/1 |
| 16 | N-100 | 0.67 | g | 3% ARQUAD 12/18 | 50/25/1 |

NOTES:
Reactions run in MIBK with the acetate buffer described in Example 1 unless noted.
Initiated with 0.3 wt percent "VAZO 67" at 90° C., complete Perfluoroalkyl Iodide Mixture A consumption in 2 hrs.
LEGEND:
Ratio is the mole ratio of diallyl amine to isocyanate, remaining isocyanate reacted with extender Solids = (concentration of polymer in solvent/concentration of solids in the dispersion/ratio of polymer solution to water in emulsion)
EXTENDER DETAIL:
a "JEFFAMINE D-400" poly[oxy(methyl-1,2-ethanyl)] alpha-(2-aminomethylethyl)-omega-(2-aminomethyl-ethoxy-CAS No. [9146-10]0 (Huntsman Chemical, Houston, TX)
b Extended with Polyacrylate A365 equivalent weight (EW) = 607 containing terminal hydroxyl groups
c Extended with Saturated polyester 670A-80 EW = 500 containing terminal hydroxyl groups
d Extended with "DESMOPHEN 1300" saturated polyester in xylene EW = 567 containing terminal hydroxyl groups
e Extended with "DESMOPHEN A-160A" Polyacrylate EW = 1058 containing terminal hydroxyl groups
All of extenders b through e are products of the Bayer Corporation, Pittsburgh, PA.

EXAMPLE 17

Into reactor 1 were placed 60 g of "DESMODUR N-100" and 400 ml MIBK. To this solution were added 18 g of allyl alcohol and 0.1 g dibutyltin dilaurate. The contents were heated at 90° C. for 2 hours. A sample of the reaction mixture was analyzed for unreacted allyl alcohol by quantitative gas chromatography and showed no (<0.5 g) unreacted allyl alcohol.

To the same reaction mass were added, 100 ml of 0.6M acetate buffer (10 g concentrated acetic acid, 10 g 50% NaOH in 80 ml water), 100 g of Perfluoroalkyl Iodide Mixture A, and 0.5 g of "VAZO 67". There was one more addition of initiator four hours later. After 8 hours heating at 90° C., analysis showed no unreacted perfluoroalkyl iodide. A phase cut was taken, the contents washed with 100 ml concentrated sodium acetate, and the total organic solution was homogenized at 3000 psig in 600 ml water with 2 g trimethyloctadecyl ammonium chloride and 2 g trimethyl-dodecyl ammonium chloride. After removing the organic solvent, the resultant dispersion was applied onto carpet at 1000 ppm fluorine and gave drum soil performance better than the untreated control.

EXAMPLE 18

The experiment in Example 1 was repeated except "DESMODUR N-3200" was used in place of "DESMODUR N-100". The reaction mass was emulsified to give 1000 g of an emulsion containing 8.8% Fluorine.

EXAMPLE 19

Reactor 1 was charged with 400 g dry methyl isobutyl ketone (MIBK), and 25 g of hexamethylene diisocyanate. To this was added slowly, 33 g (0.30 eq) of diallyl amine and the pot temperature allowed to go up to 90° C. After addition was complete, the contents were allowed to stir for 30 minutes and gas chromatographic analysis showed no unreacted diallyl amine. To the same reaction mixture was added 50 g of a dilute acetate buffer consisting of 5 g concentrated acetic acid, 5 g 50% sodium hydroxide and 40 g water, along with 150 g Perfluoroalkyl Iodide Mixture A. The contents are sparged with nitrogen and when the mixture reached 90° C. again, 0.5 g of "VAZO 67" was added. After four hours, gas chromatographic analysis showed no unreacted perfluoro alkyl iodide.

The mixture was worked-up and emulsified as described in Example 1 to give 756 g of an aqueous emulsion that contained 11.3% fluorine. It was applied to carpet to give soil-resist properties similar to the compound made in example 1.

I claim:

1. A perfluoroalkyl-substituted polyisocyanate comprising the product prepared by the sequential reaction of a polyisocyanate containing two or more reactive isocyanate groups per molecule with a terminally unsaturated alkenyl or alkynyl Zerwitinoff hydrogen-containing compound, perfluoro-alkylating the resulting alkenylated or alkynylated polyisocyanate by reaction with perfluoroalkyl iodides at a pH between 2 and 8, and dehydroiodinating the resulting perfluoroalkyl-substitured polyisocyanate so as to effect elimination of hydrogen iodide therefrom.

2. The perfluoroalkyl-substituted polyisocyanate of claim 1 wherein said polyisocyanate containing two or more reactive isocyanate groups per molecule comprises a hexamethylene diisocyanate homopolymer having the formula:

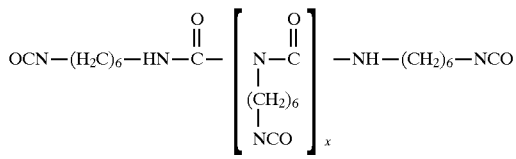

wherein x is an integer equal to or greater than 1.

3. The perfluoroalkyl-substituted polyisocyanate of claim 2 wherein x is an integer between 1 and 8.

4. The perfluoroalkyl-substituted polyisocyanate of claim 1 wherein said polyisocyanate containing two or more reactive isocyanate groups per molecule comprises a hexamethylene diisocyanate-derived isocyanurate trimer having the formula:

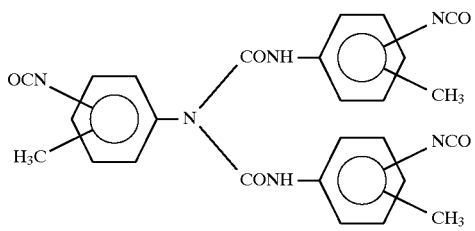

wherein $R^{12}$ is a divalent hydrocarbon group.

5. The perfluoroalkyl-substituted polyisocyanate of either claim 1, 2, 3, or 4 wherein said terminally unsaturated alkenyl or alkynyl Zerewitinoff hydrogen-containing compound is allyl amine.

6. The perfluoroalkyl-substituted polyisocyanate of either claim 1, 2, 3, or 4 wherein said terminally unsaturated alkenyl or alkynyl Zerewitinoff hydrogen-containing compound is diallyl amine.

7. The perfluoroalkyl-substituted polyisocyanate of either claim 1, 2, 3, or 4 wherein said terminally unsaturated alkenyl or alkynyl Zerewitinoff hydrogen-containing compound is allyl alcohol.

8. An aqueous emulsion comprising water, an emulsifying agent, and the perfluoroalkyl-substituted polyisocyanate of either claim 1, 2, 3, or 4.

9. An aqueous emulsion comprising the perfluoroalkyl-substituted polyisocyanate of claim 5, water and an emulsifying agent.

10. An aqueous emulsion comprising the perfluoroalkyl-substituted polyisocyanate of claim 6, water and an emulsifying agent.

11. An aqueous emulsion comprising the perfluoroalkyl-substituted polyisocyanate of claim 7, water and an emulsifying agent.

12. The perfluoroalkyl-substituted polyisocyanate of claim 1 wherein said polyisocyanate containing two or more reactive isocyanate groups per molecule is of the formula:

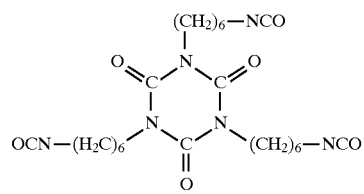

13. The perfluoroalkyl-substituted polyisocyanate of claim 1 wherein said polyisocyanate containing two or more reactive isocyanate groups per molecule is of the formula:

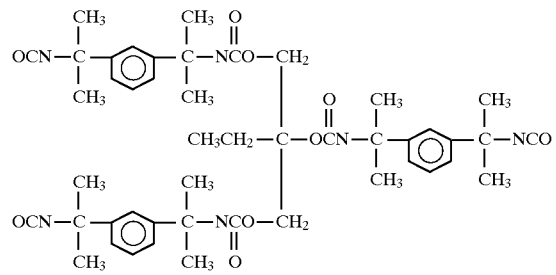

14. The perfluoroalkyl-substituted polyisocyanate of claim 12 or 13 wherein said terminally unsaturated alkenyl or alkynyl Zerewitinoff hydrogen-containing compound is selected from the group consisting of allyl amine, diallyl amine and allyl alcohol.

15. An aqueous emulsion comprising the perfluoroalkyl-substituted polyisocyanate of claim 12, water, and an emulsifying agent.

16. An aqueous emulsion comprising the perfluoroalkyl-substituted polyisocyanate of claim 13, water, and an emulsifying agent.

* * * * *